United States Patent
Imura et al.

(10) Patent No.: US 8,912,369 B2
(45) Date of Patent: *Dec. 16, 2014

(54) METHOD FOR PRODUCTION OF 1-CHLORO-3,3,3-TRIFLUOROPROPENE

(71) Applicant: Central Glass Company, Limited, Ube-shi, Yamaguchi (JP)

(72) Inventors: Hideaki Imura, Saitama (JP); Naoto Takada, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/929,244

(22) Filed: Jun. 27, 2013

(65) Prior Publication Data

US 2014/0005446 A1    Jan. 2, 2014

(30) Foreign Application Priority Data

Jun. 29, 2012  (JP) ................................ 2012-146501
Jun. 25, 2013  (JP) ................................ 2013-133059

(51) Int. Cl.
| | |
|---|---|
| C07C 17/20 | (2006.01) |
| C07C 17/25 | (2006.01) |
| C07C 19/08 | (2006.01) |
| C07C 19/10 | (2006.01) |
| C07C 21/18 | (2006.01) |
| C07C 21/04 | (2006.01) |
| C07C 17/383 | (2006.01) |
| C07C 17/357 | (2006.01) |

(52) U.S. Cl.
CPC ........... *C07C 17/357* (2013.01); *C07B 2200/09* (2013.01); *C07C 17/383* (2013.01); *C07C 17/206* (2013.01); *C07C 17/25* (2013.01)
USPC ........... 570/156; 570/227; 570/164; 570/220; 570/155; 570/226

(58) Field of Classification Search
USPC .......................... 570/155, 156, 226, 227, 228
See application file for complete search history.

(56) References Cited

U.S. PATENT DOCUMENTS

| | | | | |
|---|---|---|---|---|
| 5,202,102 | A * | 4/1993 | Nguyen | 423/240 S |
| 7,067,705 | B2 * | 6/2006 | Moscoe | 570/101 |
| 7,829,747 | B2 * | 11/2010 | Wang et al. | 570/156 |
| 8,115,037 | B2 * | 2/2012 | Sakyu et al. | 570/156 |
| 8,487,144 | B2 * | 7/2013 | Hamasaki et al. | 570/156 |
| 2009/0253820 | A1 | 10/2009 | Bowman et al. | |
| 2009/0270661 | A1 | 10/2009 | Wang et al. | |
| 2011/0052652 | A1 | 3/2011 | Suzuki et al. | |
| 2011/0172470 | A1 * | 7/2011 | Hamasaki et al. | 570/156 |
| 2011/0270001 | A1 | 11/2011 | Ishihara et al. | |
| 2013/0065044 | A1 | 3/2013 | Bowman et al. | |

FOREIGN PATENT DOCUMENTS

| | | |
|---|---|---|
| EP | 1 231 195 A1 | 8/2002 |
| JP | 2000-229894 A | 8/2000 |
| JP | 2002-047218 A | 2/2002 |
| JP | 3271005 B2 | 4/2002 |
| JP | 2005-504097 A | 2/2005 |
| JP | 3869184 B2 | 1/2007 |
| JP | 2008-19243 A | 1/2008 |
| JP | 2009-514902 A | 4/2009 |
| JP | 2009-263365 A | 11/2009 |
| JP | 2010-64990 A | 3/2010 |
| JP | 2010-100613 A | 5/2010 |
| JP | 2010-202640 A | 9/2010 |
| JP | 2011-504538 A | 2/2011 |
| WO | WO 01/36355 A1 | 5/2001 |

* cited by examiner

*Primary Examiner* — Jafar Parsa
*Assistant Examiner* — Medhanit Bahta
(74) *Attorney, Agent, or Firm* — Crowell & Moring LLP

(57) ABSTRACT

A production method of 1-chloro-3,3,3-trifluoropropene according to the present invention includes bringing a composition containing a compound of the general formula (1): $CF_3$—$CH_2$—CHClX (where X is a fluorine atom or a chlorine atom) into contact with a solid catalyst in the presence of hydrogen chloride. In this production method, the composition containing ozone depleting HCFC such as 3-chloro-1,1,1,3-tetraluoforpropane or 3,3-dichloro-1,1,1-trifluoropropane can be efficiently converted to the 1-chloro-3,3,3-trifluoropropene, which has less influence on the global environment and is useful as a solvent, a cleaning agent, a coolant, a working fluid, a propellant, a raw material for fluorinated resins etc.

5 Claims, No Drawings

METHOD FOR PRODUCTION OF 1-CHLORO-3,3,3-TRIFLUOROPROPENE

FIELD OF THE INVENTION

The present invention relates to a method for production of 1-chloro-3,3,3-trifluoropropene, which is an environment-adaptive chlorofluorocarbon useful as a solvent, a cleaning agent, a coolant, a refrigerant, a working fluid, a propellant, a raw material for fluorinated resins etc. More particularly, the present invention relates to a method for converting an ozone depleting substance, which has been a subject of regulation under the Ozone Layer Protection Law (enacted in 1988), to 1-chloro-3,3,3-trifluoropropene.

BACKGROUND OF THE INVENTION

It is known that 1-chloro-3,3,3-trifluoropropene is an environment-adaptive material that is not categorized as an ozone depleting substance and is suitably usable as a solvent, a cleaning agent, a coolant, a refrigerant, a working fluid, a propellant, a raw material for fluorinated resins etc. Herein, 1-chloro-3,3,3-trifluoropropene exists as trans and cis geometric isomers. The trans and cis isomers of 1-chloro-3,3,3-trifluoropropene are hereinafter sometimes called "1233E" and "1233Z", respectively, by their identification numbers with additional symbols. The 1-chloro-3,3,3-trifluoropropene is simply called "1233" in the case where there is no need to distinguish the trans and cis isomers or in the case where it refers to a mixture of the trans and cis isomers. Further, there is known 1,3,3,3-tetrafluoropropene as a material relevant to 1-chloro-3,3,3-trifluoropropene. Trans and cis isomers of 1,3,3,3-tetrafluoropropene are hereinafter sometimes called "1234E" and "1234Z", respectively. The 1,3,3,3-tetrafluoropropene is simply called "1234" in the case where there is no need to distinguish the trans and cis isomers or in the case where it refers to a mixture of the trans and cis isomers.

As a production method of 1233, Patent Document 1 discloses a process of synthesizing 1233 by reaction of 1,1,1,3,3-pentafluoropropane (sometimes called "245fa") and hydrogen chloride in gas phase in the presence of a solid catalyst.

As a production method of 1234, Patent Document 2 discloses a process of synthesizing 1234 by fluorination of 1,1,1,3,3-pentachloropropane (sometimes called "240fa") with hydrogen fluoride in liquid phase in the presence of an antimony catalyst.

There is however a problem that hydrogen chloride containing hydrogen fluoride is generated during the synthesis of the 245fa by the fluorination of the 240fa. As the hydrogen chloride containing hydrogen fluoride is more difficult to use than pure hydrogen chloride with no hydrogen fluoride, it is often the case that the hydrogen chloride containing hydrogen fluoride is disposed of as a waste after neutralization treatment.

Further, saturated hydrochlorofluorocarbons (sometimes called "HCFC") such as 3-chloro-1,1,1,3-tetrafluoropropane (sometimes called "244fa") and 3,3,-dichloro-1,1,1-trifluoropropane (sometimes called "243fa") may be generated as impurities during the synthesis of the 245fa by the fluorination of the 240fa as discussed in Examples of Patent Document 2.

Patent Document 3 discloses a plasma decomposition apparatus for decomposition of HCFC. Patent Document 4 discloses, as an easy combustion method of HCFC, a process of decomposing an organic or inorganic halide in the coexistence of an alkali metal compound in combustion frame.

However, for example, the complete combustion of 3-chloro-1,1,1,3-tetrafluoropropane (244fa) theoretically requires 2 mol of hydrogen per 1 mol of the 244fa and gives 6 mol of earth-warming carbon dioxide gas (see the following scheme). Although it is common practice to produce the hydrogen required for such complete combustion by a steam reforming process, the steam reforming process causes emission of carbon dioxide. It is thus hardly said that the combustion of the HCFC is an environmentally suitable treatment process.

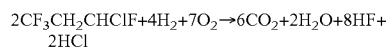

As compared to the saturated HCFC compound, 1-chloro-3,3,3-trifluoropropene (1233) has a double bond in the molecule and can be easily decomposed because of its high rate of reaction with OH radicals in the air. Accordingly, the 1233 is an environment-adaptive chlorofluorocarbon that has less influence on the ozone layer. Patent Document 5 discloses a blowing agent containing 1233 as the 1233 shows good heat insulating properties.

Patent document 6 discloses a process of producing 1233 by dehydrofluorination of 3-chloro-1,1,1,3-tetrafluoropropane (244fa) in the presence of a catalyst under the conditions sufficient for dehydrofluorination reaction. However, there occurs dehydrochlorination in parallel with the dehydrofluorination so that 1,1,1,3-tetrafluoropropene (1234) is also generated (as a by-product) in the production process. The selectivity of the 1233 is lowered due to the by-production of the 1234.

PRIOR ART DOCUMENTS

Patent Document 1: Japanese Laid-Open Patent Publication No. 2010-64990
Patent Document 2: International Patent Publication No. 2001/036355
Patent Document 3: Japanese Patent No. 3271005
Patent Document 4: Japanese Patent No. 3869184
Patent Document 5: Published Japanese Translation of International Patent Publication No. 2011-504538
Patent Document 6: Japanese Laid-Open Patent Publication No. 2009-263365

SUMMARY OF THE INVENTION

It is an object of the present invention to provide a method for efficiently producing 1-chloro-3,3,3-trifluoropropene (1233), which is an environment-adaptive chlorofluorocarbon useful as a solvent, a cleaning agent, a coolant, a refrigerant, a working fluid, a propellant, a raw material for fluorinated resins etc., from a composition containing an ozone depleting HCFC compound such as 3-chloro-1,1,1,3-tetrafluoropropane (244fa) or 3,3,-dichloro-1,1,1-trifluoropropane (243fa). It is also an object of the present invention to provide a method for effective use of hydrogen chloride containing hydrogen fluoride, which is generated during synthesis of 1,1,1,3,3-pentafluoropropane (245fa) by gas-phase or liquid-phase fluorination of 1,1,1,3,3-pentachloropropane (240fa) with hydrogen fluoride.

As a result of extensive researches, the present inventors have found that it is possible to promote conversion of an ozone depleting substance such as 3-chloro-1,1,1,3-tetrafluoropropane (244fa) or 3,3,-dichloro-1,1,1-trifluoropropane (243fa) to an environment-adaptive 1-chloro-3,3,3-trifluoropropene (1233) and thereby improve the yield of the 1233 by introducing hydrogen chloride into the reaction system and thereby bringing the ozone depleting substance 244fa or 243fa into contact with a solid catalyst in the presence of the hydrogen chloride. The ozone depleting substance 244fa or 243fa is generated as a by-product during synthesis of 1,1,1,3,3-pentafluoropropane (245fa) by gas- or liquid-phase fluorination of 1,1,1,3,3-pentachloropropane (240fa) with hydrogen fluoride. The present inventors have further found that, when hydrogen chloride containing unreacted hydrogen fluoride is generated as a by-product during the synthesis of the 245fa by gas- or liquid-phase fluorination of the 240fa with hydrogen fluoride, it is possible to make effective use of such by-produced hydrogen chloride in the above conversion reaction of the ozone depleting substance to 1-chloro-3,3,3-trifluoropropene (1233).

Namely, the present invention includes the following aspects 1 to 8.

[Inventive Aspect 1]

A production method of 1-chloro-3,3,3-trifluoropropene, comprising bringing a composition containing a compound of the general formula (1):

$CF_3—CH_2—CHClX$      (1)

(where X is a fluorine atom or a chlorine atom) into contact with a solid catalyst in the presence of hydrogen chloride.

[Inventive Aspect 2]

The production method according to Inventive Aspect 1, wherein the compound of the general formula (1) is $CF_3—CH_2—CHClF$.

[Inventive Aspect 3]

The production method according to Inventive Aspect 1 or 2, wherein the solid catalyst contains a metal fluoride or metal chloride having a bond of the formula: M-X (where M is at least one metal atom selected from the group consisting of those of atomic number 13 and atomic numbers 22 to 78; and X is a fluorine atom or a chlorine atom).

[Inventive Aspect 4]

The production method according to any one of Inventive Aspects 1 to 3, wherein the solid catalyst contains at least one metal oxide selected from the group consisting of alumina, titania, zirconia and niobia.

[Inventive Aspect 5]

The production method according to any one of Inventive Aspects 1 to 4, wherein the solid catalyst has been treated in advance by contact with hydrogen fluoride.

[Inventive Aspect 6]

The production method according to any one of Inventive Aspects 1 to 5, wherein the 1 chloro-3,3,3-trifluoropropene is produced from 1,1,1,3,3-pentachloropropane by the following steps:

forming a first composition containing 1,1,1,3,3-pentafluoropropane, the compound of the general formula (1) and hydrogen chloride by contact reaction of the 1,1,1,3,3-pentachloropropane and hydrogen fluoride;

recovering the hydrogen chloride from the first composition; and bringing a second composition containing the compound of the general formula (1) into contact with the solid catalyst in the presence of the recovered hydrogen chloride.

[Inventive Aspect 7]

The production method according to any one of Inventive Aspects 1 to 5, wherein the 1 chloro-3,3,3-trifluoropropene is produced from 1,1,1,3,3-pentachloropropane by the following steps:

forming a first composition containing 1,1,1,3,3-pentafluoropropane, the compound of the general formula (1) and hydrogen chloride by contact reaction of the 1,1,1,3,3-pentachloropropane and hydrogen fluoride;

recovering the hydrogen chloride from the first composition;

distilling a residue remaining after the recovery of the hydrogen chloride, thereby forming a second composition containing the compound of the general formula (1); and bringing the second composition into the solid catalyst in the presence of the recovered hydrogen chloride.

[Inventive Aspect 8]

The production method according to any one of Inventive Aspects 1 to 7, wherein the hydrogen chloride is in the form of an acid composition containing 0.0001 to 10 mass % of hydrogen fluoride as an impurity based on the total amount of the acid composition.

It is possible by the production method of the present invention to efficiently convert the composition containing the ozone depleting substance such as 3-chloro-1,1,1,3-tetrafluoropropane (244 fa) or 3,3,-dichloro-1,1,1-trifluoropropane (243fa) to the environment-adaptive 1 chloro-3,3,3-trifluoropropene (1233). It is also possible to use hydrogen chloride containing unreacted hydrogen fluoride, which is generated during the synthesis of 1,1,1,3,3-pentafluoropropane (245fa) by the gas-phase or liquid-phase fluorination of 1,1,1,3,3-pentachloropropane (240fa) with hydrogen fluoride, as the hydrogen chloride in the production method of the present invention. Accordingly, the production method of the present invention is an environment-friendly method that efficient production of the environment-adaptive material through the efficient use of not only the ozone depleting substance but also the hydrogen chloride containing hydrogen fluoride.

DESCRIPTION OF THE EMBODIMENTS

Hereinafter, exemplary embodiments of the present invention will be described in detail below. It is noted that: the present invention is not limited to the following embodiments; and various changes and modifications can be made to the following embodiments based on the common knowledge of those skilled in the art without departing from the scope of the present invention.

1. Production method of 1-chloro-3,3,3-trifluoropropene (1233)

In Patent Document 1,1-chloro-3,3,3-trifluoropropene (1233) is produced by contact reaction of 1,1,1-3,3-pentafluoropropane (245fa) and hydrogen chloride in gas phase in the presence of a solid catalyst as indicated in the following scheme. At this time, the hydrogen chloride is directly involved in the reaction.

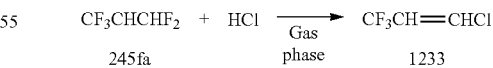

$$CF_3CHCHF_2 + HCl \xrightarrow{\text{Gas phase}} CF_3CH=CHCl$$
$$\text{245fa} \qquad\qquad\qquad\qquad \text{1233}$$

Further, 1-chloro-3,3,3-trifluoropropene (1233) is produced by using a fluorination catalyst $Cr_2O_3$ as a dechlorination catalyst and supplying 3-chloro-1,1,1,3-tetrafluoropropane (244fa) into a reaction vessel at a temperature of 350° C. in Examples 1 and 2 of Patent Document 6. It is however hardly said that the selectivity of the 1233 is high because 1,3,3,3-tetrafluoropropene (1234) is generated as a by-product in this method. In Example 3 of Patent Document 6, the conversion rate of the 244fa is at a low level of 27.3% even though the yield of the 1233 including both of 1233E and 1233Z is at a high level of 95.5%.

By contrast, there is provided a production method of 1-chloro-3,3,3-trifluoropropene (1233) according to the present invention, which includes bringing a composition containing a compound of the general formula (1): $CF_3$—$CH_2$—CHClX (where X is a fluorine atom or a chlorine atom) into contact with a solid catalyst in the presence of hydrogen chloride. The production method of the present invention is characterized in that the 1233 can be produced selectively with substantially no generation of 1234 as a by-product even though the contact reaction is performed in the presence of hydrogen fluoride.

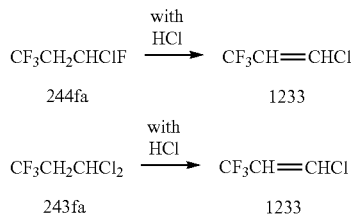

As the compound of the general formula (1), there can suitably be used $CF_3$—$CH_2$—CHClF (244fa) in the production method of the present invention.

One specific reaction example of the production method of the present invention will be explained below with reference to Scheme 1.

As indicated in Scheme 1, the production method of the present invention allows use of the ozone depleting compound of the general formula (1) such as 244fa or 234fa, which is generated during synthesis of 245fa, as a raw material for production of the environment-adaptive 1233.

The production method of the present invention also allows supply and reuse of hydrogen chloride containing unreacted hydrogen fluoride, which is generated as a by-product during fluorination of 1,1,1,3,3-pentachloropropane (240) with hydrogen fluoride, in the reaction system as indicated in Scheme 1. In order to use such by-produced hydrogen chloride as a product (commercial product), it is necessary to perform high purification treatment on the by-produced hydrogen chloride because the hydrogen fluoride is contained as an impurity in the by-produced hydrogen chloride. On the other hand, it is not easy to dispose of the by-produced hydrogen chloride as a waste because it takes much expense to perform neutralization treatment before the disposal of the by-produced hydrogen chloride. In the production method of the present invention, the hydrogen chloride containing hydrogen chloride as an impurity can be easily used and efficiently consumed.

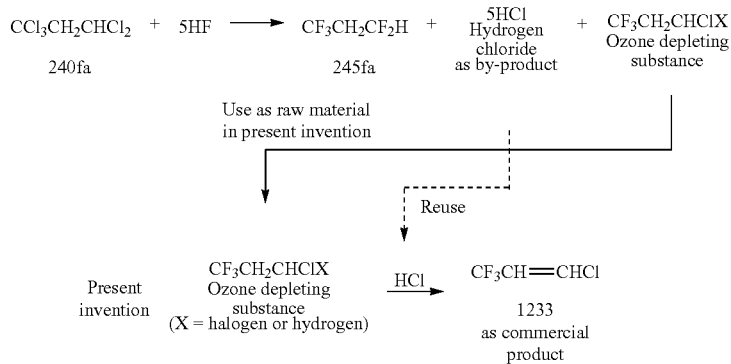

Scheme 1

It is accordingly one preferred embodiment of the present invention to produce the 1-chloro-3,3,3-trifluoropropene from 1,1,1,3,3-pentachloropropane by the following steps: forming a first composition containing 1,1,1,3,3-pentafluoropropane (245fa), the compound of the general formula (1) and hydrogen chloride by contact reaction of 1,1,1,3,3-pentachloropropane (240fa) and hydrogen fluoride; recovering the hydrogen chloride from the first composition; and bringing a second composition containing the compound of the general formula (1) into contact with the solid catalyst in the presence of the recovered hydrogen chloride.

In this way, the hydrogen chloride recovered from the first composition, which is obtained as the product of the reaction of 1,1,1,3,3-pentachloropropane (240fa) with hydrogen fluoride and contains the 1,1,1,3,3-pentafluoropropane (245fa), the compound of the general formula (1) and hydrogen chloride, can preferably be supplied into the reaction system for efficient production of the 1-chloro-3,3,3-trifluoropropene (1233) as the target product in the production method of the present invention.

It is also another preferred embodiment of the present invention to produce the 1-chloro-3,3,3-trifluoropropene from 1,1,1,3,3-pentachloropropane by the following steps: forming a first composition containing 1,1,1,3,3-pentafluoropropane (245fa), the compound of the general formula (1) and hydrogen chloride by contact reaction of the 1,1,1,3,3-pentachloropropane (240fa) and hydrogen fluoride; recovering the hydrogen chloride from the first composition; distilling a residue remaining after the recovery of the hydrogen chloride, thereby forming a second composition containing the compound of the general formula (1); and bringing the second composition into the solid catalyst in the presence of the recovered hydrogen chloride.

In the production method of the present invention, the second composition extracted by distillation of the first composition, which is obtained as the product of the reaction of 1,1,1,3,3-pentachloropropane (240fa) with hydrogen fluoride and contains the 1,1,1,3,3-pentafluoropropane (245fa), the compound of the general formula (1) and hydrogen chloride, can preferably be used as the raw material composition containing the compound of the general formula (1) for efficient production of the 1-chloro-3,3,3-trifluoropropene (1233) as the target product.

2. HCFC Compound

Next, an explanation will be given of the HCFC compound used in the production method of the present invention.

In the production method of the present invention, the HCFC compound of the general formula (1) is used as the reaction substrate. Specific examples of the HCFC compound of the general formula (1) are 3,3-dichloro-1,1,1-trifluoropropane (243fa) where X is a chlorine atom and 3-chloro-1,1,1,3-tetrafluoropropane (244fa) where X is a fluorine atom.

Although both of 3,3-dichloro-1,1,1-trifluoropropane (243fa) where X is a chlorine atom and 3-chloro-1,1,1,3-tetrafluoropropane (244fa) where X is a fluorine atom are suitably usable, the 244fa where X is fluorine is particularly suitable in the production method of the present invention. These HCFC compounds can be used solely or in the form of a mixture thereof. It suffices to use the composition as the raw material as long as the composition contains at least one compound of the above generation formula.

It is feasible to obtain the composition by any process as long as the composition contains the above-mentioned HCFC compound: $CF_3$—$CH_2$—CHClX, which can be synthesized by the gas- or liquid-phase fluorination of the 1,1,1,3,3-pentachloropropane (240fa) with hydrogen fluoride (see Scheme 1). The composition can be in the form a reaction mixture after the reaction, a simple substance isolated by distillation etc. or a composition that has been increased in content ratio by distillation etc. Preferably, the composition in which the HCFC compound has been increased in content by distillation is used as the raw material. It is alternatively feasible to purchase and use HCFC compound or HCFC-containing composition.

The composition can preferably be prepared from the 1,1,1-3,3-pentachloropropane (240fa) by the following steps: reacting the 240fa with hydrogen fluoride to form a reaction mixture containing the 245fa, HCFC and hydrogen chloride; and distilling the desired HCFC-containing composition from the reaction mixture.

The composition may contain, in addition to the saturated HCFC compound, an organic compound of the general formula: $CF_3$—CH=CHX (where X is a fluorine atom or a chlorine atom). Specific examples of the additional organic compound of the above formula are 1-chloro-3,3,3-trifluoropropene (1233), which is the target compound of the production method of the present invention, and $CF_3$—CH=CHF. The composition may further contain 1,1,1,3,3-pentafluoropropane (245fa). Any $CF_3$ group-containing containing compound obtained by the fluorination of the 1,1,1,3,3-pentachloropropane (240fa) can be a precursor of the target 1-chloro-3,3,3-trifluoropropene (1233) and thus can be contained in the composition.

3. Hydrogen Chloride

An explanation will be given of the hydrogen chloride used in the production method of the present invention.

There is no particular limitation on the grade of the hydrogen chloride. For example, the hydrogen chloride can be of industrial grade. It is alternatively feasible to use hydrogen chloride containing hydrogen fluoride (hereinafter sometimes referred to as "acid composition"), which is generated during the fluorination of the 1,1,1,3,3-pentachloropropane (240fa) with hydrogen fluoride, as the hydrogen chloride in the production method of the present invention as mentioned above.

During this fluorination, the hydrogen chloride inevitably occurs as an acid composition. Even when the hydrogen chloride is roughly distilled (by so-called rough distillation), rather than subjected to precision distillation, a small amount of hydrogen fluoride is contained in the hydrogen chloride. Unless the hydrogen chloride is purified to a high purity, the hydrogen chloride is not available as a commercial product. It is thus often the case that the hydrogen chloride is disposed of as a waste after neutralization treatment. The disposal of the hydrogen chloride is not preferred in terms of resource conservation and waste reduction. The utilization of the hydrogen chloride generated during the fluorination is desirable for the purpose of resource conservation and waste reduction.

The hydrogen chloride may be used in the form of a distillation product in the present invention. The content of the hydrogen fluoride in the hydrogen chloride is preferably 0.0001 to 10 mass %, more preferably 0.0001 to 5 mass %. It is preferable that the concentration of the hydrogen fluoride is as small as possible. Although the recovered hydrogen chloride may contain low-boiling organic substances such as fluorine-containing organic compounds, such low-boiling organic substance become a precursor of the target 1233 compound or do not get involved in the reaction. The recovered hydrogen chloride can be thus used as it is even though these organic substances are mixed in the recovered hydrogen chloride. In general, cis-1,3,3,3-tetrafluoropropene (sometimes called "1234Z"), trans-1,3,3,3-tetrafluoropropene (sometimes called "1234E") or 245fa may be mixed in the hydrogen fluoride when the hydrogen fluoride is recovered by rough distillation after the liquid-phase fluorination of the 240. The hydrogen chloride containing these compounds is usable in the present invention.

There is no particular limitation on the process for isolation of the hydrogen chloride. The hydrogen chloride can be isolated by any known process, preferably dry pressure distillation.

In order to prevent deterioration in the catalytic activity of the solid catalyst, it is feasible to add hydrogen fluoride to the hydrogen chloride intentionally and separately from the hydrogen fluoride mixed into the hydrogen chloride. At this time, the mass ratio of hydrogen chloride/hydrogen fluoride is preferably 2 or higher. The amount of generation of the earth-warming 245fa may be increased when the hydrogen fluoride is added excessively. An inert gas such as nitrogen or argon may be added when desired by one skilled in the art. In this case, however, there arises a need to perform a step of separation of the product from the inert gas.

4. Solid Catalyst

Next, an explanation will be given of the solid catalyst used in the production method of the present invention.

The solid catalyst preferably contains a fluoride or chloride of specific metal, which has a metal-halogen bond (M-X bond where M is e.g. at least one of metals of atomic numbers 13 and 22 to 79 and X is a fluorine atom or a chlorine atom).

As the metal of the solid catalyst, there can be used any of metals of Groups 4 to 15 of the periodic table in the production method of the present invention. More specifically, aluminum (atomic number 13) and transition metals of atomic numbers 22 to 78 are usable as the metal of the solid catalyst. Preferred examples of the metal of the solid catalyst are aluminum, titanium, chromium, manganese, nickel, copper, cobalt, zirconium, niobium, molybdenum, tin, antimony and tantalum. These metals can be used solely or in combination of two or more thereof. Magnesium, sodium or potassium may be added as a promoter.

One example of the solid catalyst used in the production method of the present invention is a catalyst prepared by fluorination or chlorination of a metal oxide such as alumina in such a manner that the catalyst has an active species formed with a M-X bond (e.g. Al—F bond) on a part of a surface thereof. The presence or absence of the M-X bond can be verified by instrumental analysis such as EXAFS (Extended X-ray Absorption Fine Structure), XAFS (X-ray Absorption Fine structure), XRF (X-ray Fluorescence Analysis), XPS (X-ray photoelectron spectroscopy), IR (Infrared Spectroscopy) or XRD (X-ray Diffraction). As a convenient verification technique, it is feasible to verify that the catalyst is effective in the production method of the present invention by firing the catalyst at 300° C. after the completion of the reaction, and then, detecting the metal atom and the fluorine or chlorine atom by the above analytical means.

The firing time required for removal of physically adsorbed fluorine or chlorine atom from the catalyst is about 12 to 120 hours. The physically adsorbed fluorine or chlorine atom can be removed efficiently by firing under the flow of nitrogen or under reduced pressure. Particularly preferred are XAFS and XPS, each of which enables detailed analysis of the state of the metal-fluorine bond or metal-chlorine bond. In general, the physically adsorbed halogen atom is present in the form of a hydrogen halide.

It is effective to positively fluorinate some or major portion of the metal surface by treatment with hydrogen fluoride etc. and form a metal-fluorine bond on the solid catalyst as mentioned above. In the case where the raw material composition contains a fluorine- or chlorine-containing compound as in the production method of the present invention, a metal-fluorine bond or metal-chlorine bond can be formed by contact of the raw material itself with the metal. It is thus feasible to form a metal-fluorine bond or metal-chlorine bond formed on the solid catalyst such that the reaction can be performed under the action of the resulting solid catalyst by using the metal-fluorine or metal-chlorine bond-formable raw material in combination with the metal. In this case, it is assumed that the metal-fluorine bond or metal-chlorine bond can be verified by analysis of the solid after the reaction. In the above technique where the metal-fluorine or metal-chlorine bond-containing active species is formed by introducing the ozone depleting substance as the raw material to the catalyst without positively fluorinating the metal surface by treatment with hydrogen fluoride etc., there is a possibility that the ozone depleting substance may be decomposed during the formation of the metal-fluorine bond or metal-chlorine bond on the catalyst surface by metal fluorination or chlorination treatment. For this reason, it is preferable to perform fluorination or chlorination treatment on the metal surface before the introduction of the raw material.

The size (maximum particle diameter) of the catalyst is preferably 1/30 to 1/3, more preferably 1/20 to 1/5, of the inner diameter of the reaction vessel used in the reaction. When the size of the catalyst is larger than 1/3 of the inner diameter of the reaction vessel, the raw material may pass through the reaction vessel without contacting the catalyst. There arises a possibility of increase in the pressure loss of the reaction vessel or clogging of the reaction vessel when the size of the catalyst is smaller than 1/30 of the inner diameter of the reaction vessel. More specifically, the maximum particle diameter of the catalyst is preferably in the range of 0.5 to 20 mm, more preferably 2 to 10 mm.

The catalyst can be prepared in the above size by molding the oxide or salt of any of metals of atomic numbers 13 to 78 into spherical form or pellet form. Although one skilled in the art may prepare the catalyst by pressure-molding the metal oxide or metal salt with the use of a compression molding machine, it is feasible to use commercially available pellets or balls (spheres) composed predominantly of alumina ($\gamma$-alumina, $\alpha$-alumina etc.), titania zirconia as the catalyst. Alternatively, the catalyst can be provided in the form of an impregnated catalyst by using activated carbon (coconut shell coal, charcoal, peat coal etc.) or any of these metal oxides as a carrier and impregnating the carrier with a solution of the above-mentioned effective metal component. It is preferable to subject, in advance, the carrier to fluorination treatment by hydrogen fluoride etc.

There is no particular limitation on the preparation process of the impregnated catalyst. The impregnated catalyst can be prepared by providing a solution of a soluble compound of the metal, such as nitrate, chloride or oxyhalide, impregnating a carrier with the solution or spraying the solution onto a carrier, drying the solution-applied carrier, and then, bringing the resulting metal salt-carrying carrier into contact with hydrogen fluoride, hydrogen chloride, chlorofluorohydrocarbon etc. under heating for fluorination of part or the whole of the carried metal or the carrier. A fluorination product of alumina, titania, stainless steel etc. (such as fluorinated alumina) and activated carbon are also usable as the catalyst. There is no particular limitation on the fluorination process. For example, the fluorinated alumina catalyst can be prepared by providing alumina commercially available for drying use or use as a catalyst carrier, flowing hydrogen fluoride to the alumina while heating the alumina, and thereby bringing the alumina into contact with hydrogen fluoride in gas phase, or by providing an aqueous solution of hydrogen fluoride, spraying the solution to the alumina or immersing the alumina in the solution at around room temperature, and then, drying the solution-applied alumina.

In the case of where the metal compound is liquid at around room temperature, such as antimony pentachloride, tin tetrachloride or titanium tetrachloride, the solid catalyst may be prepared by impregnating the metal compound as it is into the activated carbon, alumina etc.

Regardless of whether the catalyst is prepared by any process, it is preferable to active the catalyst by contact with hydrogen fluoride or another fluorinating agent such as fluorine-containing hydrocarbon before use.

Especially suitable examples of the catalyst are alumina, titania, zirconia, niobia, chromium activated carbon, nickel/activated carbon, iron/activated carbon, antimony/activated carbon, chromium/alumina and chromium/zirconia. Among others, preferred is a catalyst that contains at least one selected from the group consisting of alumina, titania, zirconia and niobia and has been subjected to fluorination treatment with hydrogen fluoride. Particularly preferred in the present invention is a catalyst that contains alumina and has been subjected to fluorination treatment with hydrogen fluoride.

5. Reaction Conditions

The reaction conditions of the production method of the present invention will be next explained below.

The reaction can be performed in a gas-phase flow system in the production method of the present invention. Specific examples of the reaction system are a fixed-bed flow system, a fixed-bed circulation system, a fluidized-bed flow system or the like. Among others, it is convenient to adopt a fixed-bed gas-phase flow system. Further, it is convenient to perform the reaction at around normal pressure (i.e. under atmospheric pressure conditions) although the reaction can be performed under reduced pressure conditions or under pressurized conditions.

The HCl/composition ratio in the production method of the present invention will be explained below. Herein, the HCl/composition ratio refers to the ratio of the mass of the hydrogen chloride to the mass of the composition. The HCl/composition ratio is preferably in the range of 0.1 to 30, more preferably 0.5 to 20. When the HCl/composition ratio is smaller than 0.1, there may occur an unfavorable result such as insufficient conversion to 1-chloro-3,3,3-trifluoropropene (1233), accelerated caulking of the catalyst by organic substance, early secular deterioration of the catalyst etc. There may also occur an unfavorable result such as increase in the load of recovery of the hydrogen chloride from the reaction product or deterioration in the productivity of the 1233 when the HCl/composition ratio is larger than 30.

In the production method of the present invention, the reaction temperature is varied depending on the kind and state of the solid catalyst, the contact time etc. and is preferably in the range of 200 to 400° C., more preferably 250 to 350° C. When the reaction temperature is lower than 200° C., the conversion rate may be lowered. There may occur an unfavorable result such as increase in side reaction, caulking etc. when the reaction temperature is higher than 400° C.

The contact time between the composition and the solid catalyst in the reaction is varied depending on the kind of the reaction composition etc. and is generally in the range of 0.1 to 200 seconds, preferably 2 to 150 seconds. When the contact time is shorter than 0.1 second, there arises a possibility of low conversion or increase in pressure loss.

In the case where the solid catalyst is deteriorated in catalytic activity or deactivated during the progress of the reaction, it is feasible to remove caulking substance from the surface of the solid catalyst by contact oxidation with air or chlorine under temperature conditions of 250 to 800° C. At this time, there may occur sudden generation of heat when the oxidation treatment is performed with the use of only air or chlorine. It is thus preferable to perform the oxidation treatment while diluting such oxidation gas with nitrogen etc. for safety purposes. It is also preferable in the oxidation treatment to control the rate of dilution of the oxidation gas with the nitrogen etc. by checking the temperature of the heat spot in the reaction vessel. After the oxidation treatment, the solid catalyst is preferably subjected to fluorination or chlorination by contact with hydrogen fluoride or hydrogen chloride. In the production method of the present invention, the introduction of hydrogen chloride is effective in preventing activity deterioration or deactivation of the solid catalyst during the progress of the reaction and maintaining the catalytic activity of the solid catalyst.

In the gas-phase flow system, the 1233 can be easily recovered as the target compound by cooling the reaction vessel. The cooling temperature is preferably −80 to 5° C. There are not only a need to provide special refrigerator equipment, but also a possibility of solidification of the product, when the cooling temperature is lower than −80° C. The recovery efficiency may be lowered when the cooling temperature is higher than 5° C. It is preferable to remove fluorine ions or chlorine ions from the collected product by washing with water or an aqueous basic solution. The washing operation can be performed in a batch process or a continuous process. There may occur heat of neutralization when the washing operation is performed with the use of the aqueous alkaline solution. It is thus recommendable to first wash away the major portion of the chlorine or fluorine ions by water from the product, wash the product with the aqueous alkaline solution, and then, wash away the alkaline component by water from the product. Further, it is preferable to dry the washed product with a solid dehydrating agent such as zeolite.

In view of the fact that most organic substances get decomposed in a temperature range of 200 to 300° C., there is a possibility that high-temperature reaction such as that of the present invention may cause decomposition or unexpected reaction of raw material or reaction product and thereby generate any impurity by-product difficult to separate by distillation purification. As high purity is required for use of the 1233 as a working fluid, a cleaning agent, a solvent, a blowing agent etc., it is impossible to commercially adopt the reaction accompanied by the generation of the difficult-to-separate by-product even when the reaction yield of the 1233 is high. In the production method of the present invention, 1-chloro-3,3,3-trifluoropropene (1233) can be produced at a high purity, with substantially no generation of any material difficult to separate by distillation, under the above-mentioned preferable reaction conditions.

There is no particular limitation on the distillation column used for distillation of the 1233 as the target product in the production method of the present invention. The theoretical plate number of the distillation column is preferably 10 to 30. When the theoretical plate number is less than 10, the distillation yield may be low. The distillation purification can be performed with no particular problem when the theoretical plate number exceeds 10. In this case, however, the distillation column may become high in equipment cost and running cost. As the boiling point of the 1233E is 19° C., the coolant temperature of the distillation column is generally −50 to 5° C., preferably −20 to 0° C. When the coolant temperature is lower than −50° C., the distillation column needs to be provided with special cooling equipment and becomes high in running cost. When the coolant temperature is higher than 5° C., there increases a distillation loss unless the distillation operation is performed under pressurized conditions.

For use of the 1233 as a working fluid, a cleaning agent, a solvent, a blowing agent etc., it is necessary to control not only the organic purity but also the fluorine ion concentration, chlorine ion concentration and moisture content of the 1233. In the case of using the 1233 as a working fluid for any equipment, the fluorine ion, chlorine ion or moisture content may become a cause of corrosion of the equipment. In the case of using the 1233 as a cleaning agent for metal parts, the fluorine ion, chlorine ion or moisture content may become a cause of corrosion of the metal parts. In the case of using the 1233 as a blowing agent, the fluorine ion, chlorine ion or moisture content may react with an amine catalyst and cause a poisoning substance. In other words, the 1233 is of quality suitable for use as a working fluid, a cleaning agent, a solvent, a blowing agent etc. when the purity of the 1233 is high and, at the same time, the fluorine ion concentration, chlorine ion concentration and moisture content of the 1233 are low. In general, the purity of the 1233 is preferably 99% or higher, more preferably 99.5% or higher. The content of moisture in the 1233 is preferably 100 ppm or less, more preferably 30 ppm or less. The content of the acidic component such as hydrogen fluoride or hydrogen chloride in the 1233 is preferably 5 ppm or less, more preferably 0.5 ppm or less.

EXAMPLES

The present invention will be described in more detail below by way of the following examples. It is noted that the following examples are illustrative and are not intended to limit the present invention thereto.

Example 1

Provided was a reaction vessel of stainless steel (SUS316) equipped with a carburetor and having an inner diameter of 23 mm and a length of 400 mm. This reaction vessel was packed with 50 ml of spherical alumina particles (product name: KHS-46 manufactured by Sumika Alchem Co., Ltd.) as a catalyst. The temperature of the carburetor and the temperature of the reaction vessel were each controlled to be 150° C. while flowing nitrogen at a flow rate of 20 ml/min into the reaction vessel. Upon confirming that the temperature was stabilized at 150° C., hydrogen fluoride was fed into the reaction vessel at 0.1 to 0.2 g/min for 3 hours. After that, the temperature of the reaction vessel was raised by 30° C. every 3 hours up until the temperature of the reaction vessel reached 360° C. When the temperature of the reaction vessel reached 360° C., the feed rate of the hydrogen fluoride was increased to 0.5 g/min. In such a state, the feeding of the hydrogen fluoride was kept for 3 hours. The feeding of the hydrogen fluoride was stopped when local heat generation (heat spot) was observed during this treatment operation. The feed rate of the hydrogen fluoride was gradually increased upon confirming that the temperature was lowered to a target degree. After the above treatment operation, the feeding of the hydrogen fluoride was stopped. While flowing nitrogen at a flow rate 50 ml/min, the temperature of the carburetor and the temperature of the reaction vessel were controlled to be 180° C. and 200° C., respectively. The reaction vessel was maintained in this state for 2 hours. The flow of the nitrogen was stopped. Then, commercially available 3-chloro-1,1,1,3-tetrafluoropropane (244fa, purity: 99.30%) and hydrogen chloride were supplied into the reaction vessel at a rate of 0.2 g/min and at a rate of 270 ml/min, respectively. After the reaction reached a steady state, the outlet gas from the reaction vessel was analyzed by a chromatograph (with a FID detector). The results of gas chromatographic analysis of the outlet gas are indicated in TABLE 1. There occurred substantially no generation (by-production) of trans-1,1,1,3-tetrafluoropropene or cis-1,1,1,3-tetrafluoropropene. the total yield of the cis- and trans-1-chloro-3,3,3-trifluoropropene was 81.28%; and the conversion rate of the 244fa was 94.96%. It was thus confirmed that the 244fa was efficiently converted to the 1233.

Examples 2-3

Experimental reaction was conducted under the same conditions as in Example 1, except for changing the reaction temperature, the hydrogen chloride/composition ratio and the contact time as indicated in TABLE 1. The results of gas chromatographic analysis of the outlet gas are indicated in TABLE 1. There occurred substantially no generation (by-production) of trans-1,1,1,3-tetrafluoropropene or cis-1,1,1,3-tetrafluoropropene even under the conditions of these examples. In particular, in Example 2, the total yield of the cis- and trans-1-chloro-3,3,3-trifluoropropene was 90.48%; and the conversion rate of the 244fa was 95.1%. It was thus confirmed that the 244fa was efficiently converted to the 1233.

Example 4

Experimental reaction was conducted under the same conditions as in Example 2, except for using hydrogen chloride containing 2.3 mass % of hydrogen fluoride and changing the hydrogen chloride/composition ratio and the contact time as indicated in TABLE 1. The reaction results are indicated in TABLE 1. The reaction results of this example were substantially equivalent to those of Example 2.

Comparative Example

Experimental reaction was conducted under the same conditions as in Example 2, except for stopping the supply of hydrogen chloride into the reaction system, in order to verify the effect of the hydrogen chloride. It was confirmed by composition analysis of the outlet gas that there occurred generation (by-production) of trans-1,1,1,3-tetrafluoropropene (1234E), 1,1,1,3,3-pentafluoropropane (245fa) and the like. The yield of the 1233E in this comparative example was equal to or less than half the yield of the 1233E in Examples 1 to 4.

TABLE 1

|  | Reaction temperature (° C.) | HCl/composition ratio | Contact time (s) |
|---|---|---|---|
| Raw material |  |  |  |
| Example 1 | 250 | 9.25 | 9.92 |
| Example 2 | 300 | 9.89 | 9.98 |
| Example 3 | 350 | 9.85 | 9.98 |
| Example 4 | 300 | 9.99 | 9.96 |
| Comparative Example | 300 | — | 10.04 |

|  | GC area % | | | | | | | |
|---|---|---|---|---|---|---|---|---|
|  | 1234E | 245fa | 1234Z | 1233E | 244fa | 1233Z | 1223 | 243fa |
| Reaction raw material |  | 0.28 | 0.01 | 0.00 | 99.30 | 0.20 | 0.14 | 0.01 |
| Example 1 | 0.25 | 1.10 | 0.04 | 73.25 | 5.04 | 8.03 | 0.15 | 11.48 |
| Example 2 | 0.41 | 0.53 | 0.06 | 80.65 | 1.15 | 9.83 | 1.33 | 4.84 |
| Example 3 | 0.57 | 0.51 | 0.11 | 73.63 | 0.96 | 10.48 | 9.04 | 2.66 |
| Example 4 | 0.78 | 0.56 | 0.07 | 80.71 | 1.07 | 9.12 | 1.26 | 4.71 |
| Comparative Example | 3.72 | 14.87 | 0.96 | 37.13 | 32.60 | 7.44 | 0.12 | 3.00 |

1234E (trans-1,1,1,3-tetrafluoropropene)

TABLE 1-continued

245fa (1,1,1,3,3-pentafluoropropane)
1234Z (cis-1,1,1,3-tetrafluoropropene)
1233E (trans-1-chloro-3,3,3-trifluoropropene)
244fa (3-chloro-1,1,1,3-tetrafluoropropane)
1233Z (cis-1-chloro-3,3,3-trifluoropropene)
243fa (3,3,-dichloro-1,1,1-trifluoropropane)

Example 5

Experimental reaction was conducted for 24 hours in the same manner as in Example 1. The resulting product was collected in a cylinder of stainless steel (SUS304) cooled by a dry ice trap. The recovered product was washed three times by a reparatory funnel with ice water and dried by a molecular Sieve™, thereby yielding 150 g of product composition containing 243fa (11.61%) (see TABLE 2: "Reaction raw material"). The results of gas chromatographic analysis of the product composition are indicated in TABLE 2. Using this composition, experimental reaction was further conducted in the same manner as in Example 1 except for except for changing the reaction temperature, the hydrogen chloride/composition ratio and the contact time as indicated in TABLE 2. The reaction results are indicated in TABLE 2. It was confirmed that 3,3-dichloro-1,1,1-trifluoropropene (243fa) was also converted to the target 1-chloro-3,3,3-trifluoropropene (1233).

TABLE 2

| | Reaction temperature (° C.) | HCl/composition ratio | Contact time (s) |
|---|---|---|---|
| Reaction raw material | | | |
| Example 5 | 300 | 1 | 2.0 |

| | GC area % | | | | | | | |
|---|---|---|---|---|---|---|---|---|
| | 1234E | 245fa | 1234Z | 1233E | 244fa | 1233Z | 1223 | 243fa |
| Raw material | 0.01 | 0.71 | 0.03 | 73.51 | 5.53 | 8.12 | 0.16 | 11.61 |
| Example 5 | 0.11 | 0.41 | 0.02 | 85.33 | 0.01 | 9.72 | 0.98 | 0.19 |

1234E (trans-1,1,1,3-tetrafluoropropene)
245fa (1,1,1,3,3-pentafluoropropane)
1234Z (cis-1,1,1,3-tetrafluoropropene)
1233E (trans-1-chloro-3,3,3-trifluoropropene)
244fa (3-chloro-1,1,1,3-tetrafluoropropane)
1233Z (cis-1-chloro-3,3,3-trifluoropropene)
243fa (3,3,-dichloro-1,1,1-trifluoropropane)

Example 6

Experimental reaction was conducted for 96 hours in the same manner as in Example 2. The resulting product was collected and washed in the same manner as in Example 5. The thus-obtained sample was distilled by a distillation column with a theoretical plate number of 20, thereby yielding 492 g of a distillation fraction of 99.8% purity 1-chloro-3,3,3-trifluoropropene (1233E). The moisture content of the distillation faction was determined by Karl Fischer's method to be 7 ppm. In order to confirm the acidic component content of the distillation fraction, 100 g of the distillation fraction was extracted with 100 g of ion-exchanged water, subjected to degassing and analyzed by ion chromatography. The fluorine ion concentration of the distillation fraction was 250 ppm; and the chlorine ion concentration of the distillation fraction was 160 ppm.

Example 7

The distillation fraction of high purity 1-chloro-3,3,3-trifluoropropene (1233E) obtained in Example 10 was stored in a refrigerator (temperature: 10° C.). Then, 100 g of the distillation fraction was sampled and put into an ultrasonic cleaning system. In this cleaning system, a glass lens with fingerprints was subjected to cleaning for 100 seconds. After the cleaning, the glass lens was dried for 60 seconds by a drier. It was confirmed by visual observation of the glass lens that the fingerprints were cleaned off Example 8

Using a distillation fraction between 38 to 41° C. (50 g, main component: 1233Z) in the distillation operation of Example 6, the same experiment as that of Example 7 was conducted. It was confirmed that the fingerprints were also cleaned off from the glass lens. Further, there was seen no stain on the glass lens.

As is seen from the results of Examples 6 to 8, the 1-chloro-3,3,3-trifluoropropene (1233) obtained by distillation purification was of quality suitable for use as a working fluid, a cleaning agent, a blowing agent etc.

The invention claimed is:
1. A method for producing 1-chloro-3,3,3-trifluoropropene, comprising:
    forming a first composition containing 1,1,1,3,3-pentafluoropropane, $CF_3—CH_2—CHClF$, and hydrogen chloride by reacting 1,1,1,3,3-pentachloropropane and hydrogen fluoride;
    recovering the hydrogen chloride from the first composition;
    distilling a residue remaining after the recovery of the hydrogen chloride, thereby forming a second composition containing $CF_3—CH_2—CHClF$; and
    bringing the second composition into contact with a solid catalyst in the presence of the recovered hydrogen chloride.

2. The method according to claim 1, wherein the solid catalyst contains a metal fluoride or metal chloride having a bond of the formula: M-X, (wherein M is at least one metal atom selected from the group consisting of those of atomic number 13 and atomic numbers 22 to 78; and X is a fluorine atom or a chlorine atom.

3. The method according to claim 1, wherein the solid catalyst contains at least one metal oxide selected from the group consisting of alumina, titania, zirconia and niobia.

4. The method according to claim 1, wherein the solid catalyst has been treated in advance by contact with hydrogen fluoride.

5. The method according to claim 1, wherein the hydrogen chloride is in the form of an acid composition containing 0.0001 to 10 mass % of hydrogen fluoride as an impurity based on the total amount of the acid composition.

* * * * *